United States Patent [19]

Fujita et al.

[11] 4,320,040
[45] Mar. 16, 1982

[54] METHOD FOR PREPARING HIGHLY ABSORBENT HYDRO-GEL POLYMERS

[75] Inventors: Fumio Fujita, Takatsuki; Shuji Kitamura, Ibaraki; Toshifumi Tamura; Tsuneyuki Nagase, both of Takatsuki, all of Japan

[73] Assignee: Sumitomo Chemical Company, Limited, Osaka, Japan

[21] Appl. No.: 160,451

[22] Filed: Jun. 18, 1980

Related U.S. Application Data

[63] Continuation-in-part of Ser. No. 69,078, Aug. 23, 1979, abandoned.

[30] Foreign Application Priority Data

Sep. 7, 1978 [JP] Japan ................................ 53/110451
Sep. 13, 1978 [JP] Japan ................................ 53/113376

[51] Int. Cl.$^3$ ..................... C08L 29/04; C08L 33/02
[52] U.S. Cl. .................................. 524/459; 525/59; 524/916
[58] Field of Search ............... 525/59; 260/29.6 WA

[56] References Cited

U.S. PATENT DOCUMENTS

| | | | |
|---|---|---|---|
| 3,272,749 | 9/1966 | Martin | 252/8.5 |
| 3,935,099 | 1/1976 | Weaver et al. | 210/43 |
| 4,102,842 | 7/1978 | Fujimoto et al. | 260/29.6 PT |
| 4,124,748 | 11/1978 | Fujimoto et al. | 526/8 |

FOREIGN PATENT DOCUMENTS

| | | |
|---|---|---|
| 698712 | 3/1967 | Belgium . |
| 6913412 | 6/1970 | Netherlands . |
| 7300074 | 5/1973 | Netherlands . |

*Primary Examiner*—Carman J. Seccuro
*Attorney, Agent, or Firm*—Cushman, Darby & Cushman

[57] ABSTRACT

A method for producing a hydrophilic gel comprising polymerizing acrylic acid and/or methacrylic acid in the presence of polyvinyl alcohol to obtain a polymer (A) which is then subjected to neutralization followed by heat treatment or to heat treatment followed by neutralization, or polymerizing a neutralized product of acrylic acid and/or methacrylic acid in the presence of polyvinyl alcohol to obtain a polymer (B) which is then subjected to heat treatment, wherein said polymerization is carried out in an aqueous solution having a total concentration of acrylic acid and/or methacrylic acid or its neutralized product (the weight of the neutralized product is converted to the acid basis) and polyvinyl alcohol of 10 to 60% by weight, said heat treatment temperature is 50° to 150° C., and the weight ratio of polyvinylalcohol is acrylic acid and/or methacrylic acid or its salt (the weight of the neutralized product is converted to the acid basis) is 5 to 95: 95 to 5.

16 Claims, No Drawings

METHOD FOR PREPARING HIGHLY ABSORBENT HYDRO-GEL POLYMERS

This application is a continuation-in-part of our prior U.S. application Ser. No. 69,078, filed Aug. 23, 1979 now abandoned.

The present invention relates to a method for producing hydrophilic gels having an ability to absorb a large quantity of water. More particularly, the present invention relates to a method for producing hydrophilic gels which can preferably be used as water-absorbent materials or gel materials used in a hydrated, swollen state. The term "hydrated" referred to herein means "contain water" hereinafter.

As application of hydrophilic polymer materials to the medical industry, food industry or agricultural fields has recently advanced, particularly water-insoluble and water-absorbing hydrophilic gels have begun to be used as materials for separation and purification such as membranes and carriers for liquid chromatography, as enzyme supporting materials, as culturing materials for microorganisms or plants, as medical materials such as contact lens and suture-protective materials, and as materials requiring water absorbability and water retentivity.

Among those uses, particularly in the application fields which make use of water absorbability and water retentivity, it is desired for the hydrophilic gels to absorb as large an amount of water as possible in a short period of time when they are brought into contact with water.

The well-known methods for producing such hydrophilic gels are, for example, crosslinking of water-soluble polymers with a crosslinking agent, or modifying the water-soluble polymers to water-insoluble ones by partial substitution of the hydrophilic groups with hydrophobic ones. Hitherto, there have been proposed some materials which are made of natural or synthetic polymer substances, for example crosslinked products of polyethylene oxide, polyacrylic acid, polyvinyl pyrrolidone, sulfonated polystyrene or sodium polyacrylate; cellulose derivatives; polyacrylonitrile; and saponified products of starch-acrylonitrile graft copolymers.

However, with the exception of the saponified products of starch-acrylonitrile graft copolymers and those of copolymers of a vinyl ester, an ethylenically unsaturated carboxylic acid or its derivative, and optionally ethylene, which were previously proposed by the present inventors, these materials are low in water-absorbing ability so that they are unsatisfactory as a water-absorbent material.

Even the saponified products of starch-acrylonitrile graft copolymers having a relatively high water-absorbing ability, however, have some drawbacks in a practical use. For example, the methods for producing them are relatively troublesome although various improvements have been made, and there is a fear that when they are used in a hydrated state for a long time, the starch component rots and the gel structure is broken.

Further generally, the conventional high water-absorbent hydrophilic gels show flexibility in a moderately humid state, but in a dry state they lose flexibility to an extreme degree and show brittleness.

Consequently, they are very easy to break when handled in a dry state, and in uses requiring contact with human body, they are poor in adhesion to the skin and very unpleasant to the touch because of the poor flexibility.

The saponified products of copolymers of a vinyl ester, an ethylenically unsaturated carboxylic acid or its derivative, and optionally ethylene, which were previously proposed by the inventors, are hydrophilic gels which are free from those drawbacks and water-insoluble, have an ability to rapidly swell by contact with water and to hold a large quantity of water, and besides have excellent flexibility even in a dry state. In producing said saponified products, however, saponification of the vinyl ester units in the copolymers is essential so that improvements in production are required from the economical point of view.

It is well known that gels are obtained by mixing polyvinyl alcohol and polyacrylic acid, but those having a high water absorbability and a moderate gel strength are not yet obtained.

Further, Dutch Pat. No. 6,913,412 and U.S. Pat. No. 3,272,749 disclose methods for producing neutralized products of methacrylic or acrylic polymer grafted on polyvinyl alcohol. In these methods, however, since the polymerization is carried out in an aqueous solution of low concentration of monomer and polyvinyl alcohol or of low weight ratio of polyvinyl alcohol to monomer, the produced product is water soluble. Accordingly, a hydrophilic gel can not be obtained.

For the reasons as described above, the present inventors studied a method for producing hydrophilic gels, cheaply and simply, having a high water absorbability and a sufficient gel strength, and thus attained to the present invention.

An object of the present invention is to provide a method for producing hydrophilic gels cheaply and simply.

Another object of the present invention is to provide a method for producing hydrophilic gels which includes no saponification of vinyl ester units. A further object of the present invention is to provide a method for producing hydrophilic gels having an ability to rapidly absorb a large quantity of water. Other objects and advantages will become apparent from the following description.

According to the present invention, there is provided a method for producing highly water-absorbent hydrophilic gels comprising polymerizing 5 to 95 parts by weight of acrylic acid and/or methacrylic acid in the presence of 95 to 5 parts by weight of polyvinyl alcohol in an aqueous solution having the total concentration of said acrylic acid and/or methacrylic acid and polyvinyl alcohol of at least 10% by weight to obtain a polymer which is then subjected to neutralization followed by heat treatment or to heat treatment followed by neutralization, or polymerizing 5 to 95 parts by weight of a salt of acrylic acid and/or methacrylic acid (the weight of the salt is converted to the acid basis) in the presence of 95 to 5 parts by weight of polyvinyl alcohol in an aqueous solution having the total concentration of the salt of acrylic acid and/or methacrylic acid (the weight of the salt in converted to the acid basis), and polyvinyl alcohol of at least 10% by weight to obtain a polymer which is then subjected to heat treatment.

In the method of the present invention, it is essential to apply heat treatment at a temperature of 50° to 150° C. to the polymer and besides, before or after polymerization, to neutralize the carboxylic acid group of acrylic acid or methacrylic acid into a salt. When the monomer used as starting material is acrylic acid and/or methacrylic acid, the resulting polymer is subjected to heat treatment and neutralization, either of which may be applied first. While when the monomer is a salt of the acid previously produced by neutralization, the heat treatment only will do.

The present invention will be illustrated in detail.

The well-known polymerization techniques are applied to polymerize acrylic acid and/or methacrylic acid, or its salt in the presence of polyvinyl alcohol in an aqueous medium. In general, the polymer is synthesized by radical polymerization using a polymerization technique such as solution polymerization, emulsion polymerization (water-in-oil emulsion) or suspension polymerization (water-in-oil suspension). In emulsion or suspension polymerization, spherical polymers are obtained by polymerizing acrylic acid and/or methacrylic acid, or its salt in an aqueous solution of polyvinyl alcohol dispersed in a water-insoluble organic solvent (e.g. toluene, hexane) not dissolving the produced polymer as a dispersion medium under stirring. In this case, dispersion stabilizers and surface active agents may be used together. In this case, graft polymerization sometimes occurs.

In the present invention, the concentration of the total of said monomer and polyvinyl alcohol in the aqueous solution is limited to 10 to 60% by weight. When the concentration is less than 10% by weight, the obtained polymer becomes water soluble even if the heat treatment was carried out. Consequently a gel is not produced. When the concentration is more than 60% by weight, polymerization is hardly operable. Preferably, the concentration is 12 to 50% by weight.

In the present invention, the degree of polymerization of polyvinyl alcohol is not particularly limited, but preferably it is 200 to 10,000. Also, the degree of saponification of the polyvinyl alcohol is not particularly limited, but preferably it is 65 to 100 mole %. The weight ratio of polyvinyl alcohol to acrylic acid or methacrylic acid or its salt of the polymer is within a range of 5 to 95:95 to 5, preferably 10 to 90:90 to 10, more preferably 12 to 88:88 to 12 (the weight of the salt is converted to the acid basis).

When the weight ratio of polyvinyl alcohol to acrylic acid and/or methacrylic acid or its salt is 5:95 or less, the obtained polymer is water soluble or inferior in strength of gel even if heat treatment is carried out.

In the polymerization of acrylic acid and/or methacrylic acid, or its salt in the presence of polyvinyl alcohol, polymerization and crosslinking may be carried out at the same time by adding a well-known crosslinking agent having at least two polymerizable unsaturated linkages. As such crosslinking agent, there may be given for example polyallyl compounds (e.g. diallyl phthalate, diallyl maleate, diallyl terephthalate, triallyl cyanurate, triallyl phosphate) and polyvinyl compounds (e.g. divinylbenzene, N,N'-methylenebis(acrylamide), ethylene glycol diacrylate, ethylene glycol dimethacrylate, glycerin trimethacrylate).

The amount of crosslinking agent used depends upon the kind of the agent, but generally it is within a range of 0.001 to 20 mole %, preferably 0.01 to 10 mole %, based on the total amount of the monomer to be polymerized in the presence of polyvinyl alcohol.

As an initiator, the well-known radical initiators may be used. For example, there may be given azonitriles (e.g. azobisisobutylonitrile), alkyl peroxides (e.g. tert-butyl peroxide, cumene hydroperoxide), dialkyl peroxides (e.g. di-tert-butyl peroxide), acyl peroxides (e.g. acetyl peroxide, lauroyl peroxide, stearoyl peroxide, benzoyl peroxide), peroxy esters (e.g. tert-butyl peroxyacetate, tert-butyl peroxyisobutyrate, tert-butyl peroxypivalate), ketone peroxides (e.g. methyl ethyl ketone peroxide, cyclohexanone peroxide), hydrogen peroxide, ammonium persulfate, potassium persulfate and cerium (IV) salts. Particularly, water-soluble initiators such as hydrogen peroxide, ammonium persulfate, potassium persulfate and cerium (IV) salts are preferred. The amount of initiator added is generally 0.0001 to 5 mole % based on the total amount of the monomer.

The polymerization may be carried out by ultraviolet ray, radiation or ultrasonic wave irradiation. But the use of initiators is more general. The polymerization conditions are not also particularly limited, but the polymerization temperature is 200° C. or less, generally 10° to 100° C. The polymerization pressure is not particularly limited.

In the present invention, the salt of acrylic acid and/or methacrylic acid is polymerized in the presence of polyvinyl alcohol, followed by heat treatment, or acrylic acid or methacrylic acid is polymerized in the presence of polyvinyl alcohol, followed by heat treatment and alkali neutralization in optional order. It is desirable that the carboxylic acid group of said salt or the neutralized product of the polymerized acid is represented by the formula,

wherein $R_1$ is a sodium or potassium atom, or

(in which $R_2$, $R_3$, $R_4$ and $R_5$ are each a hydrogen atom, $C_1$–$C_4$ alkyl or alkanol group, phenyl group or $C_7$–$C_8$ aralkyl or aryl group, and at least one of them is a hydrogen atom) or

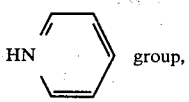 group, among which sodium, potassium and $NH_4$ are particularly preferred and sodium is most preferred.

The alkali used for neutralization is a compound corresponding to the above salts, for example sodium hydroxide, potassium hydroxide, ammonia and organic amines. The organic amines include for example methylamine, dimethylamine, trimethylamine, ethylamine, diethylamine, triethylamine, n-propylamine, isopropylamine, di-n-propylamine, diisopropylamine, tri-n-propylamine, tri-isopropylamine, tert-butylamine, n-butylamine, isobutylamine, di-tert-butylamine, di-n-butylamine, di-isobutylamine, tri-tert-butylamine, triisobutylamine, tri-n-butylamine, monoethanolamine, diethanolamine, triethanolamine, monoisopropanolamine, diisopropanolamine, triisopropanolamine, cyclohexylamine, benzylamine, aniline and pyridine. In carrying out the neutralization, solvents may be or may not be used. The neutralization conditions are not particularly limited and same as in the common neutralization of a carboxylic acid group, but the temperature is preferably 200° C. or less, particularly preferably 0° to 50° C. The reaction pressure is not also particularly limited. The amount of alkali used is preferably 0.3 to 2 times, more preferably 0.4 to 1.5 times, based on the theoretical amount.

As specific examples of the salt of acrylic acid or methacrylic acid used as monomer, there may be given sodium acrylate, sodium methacrylate, potassium acrylate, potassium methacrylate, ammonium acrylate, ammonium methacrylate, trimethylamine salt of acrylic acid or methacrylic acid, triethylamine salt of acrylic acid or methacrylic acid, and tri-n-propylamine or tri-n-butylamine salt of acrylic acid. These salts may be copolymerized together with a small amount of acrylic acid or methacrylic acid.

The heat treatment is carried out for obtaining gels having a desired water absorption ability and strength.

The temperature and period of time for the heat treatment may properly be determined taking into account the required water absorption ability and strength of the gel. In general, however, the temperature is preferably within a range of 50° to 150° C., more preferably 60° to 120° C., and the period of time is preferably within a range of about 0.5 minute to about 20 hours, more preferably 30 minutes to 8 hours. The heat treatment may be carried out (1) immediately after substantial completion of the polymerization or completion of the neutralization, (2) after the polymer or its neutralized product is separated from the system or simultaneously with drying after the separation.

The hydrophilic gels of the present invention obtained by the above methods generally have an ability to absorb water of more than 100 times as much as their own weight, as described first. When water to be absorbed contains a substance, however, the ability generally varies with the kind and amount of the substance. For example, referring to the ability to absorb water having different pH values, the gels have the highest ability when the pH of water is 8 to 10, absorbing water of more than 500 times as much as their own weight. The ability markedly reduces in the pH range of less than 5. But the water-absorbing ability once lost in an acidic liquor can be recovered in full, when the gel is transferred from the acidic water to an alkali water. Further, highly hydrated gels release a large quantity of water when a salt such as sodium chloride is added to the gels. In other words, the gels show a water absorption/water release reversible change depending upon the pH value and salt concentration of water.

Further, the hydrophilic gels of the present invention have a relatively superior flexibility even in a dry state, and therefore they are remarkably improved in touch as compared with the conventional ones.

The highly water-absorbent hydrophilic gels of the present invention have the following advantages. Firstly, the hydrophilic gels are transparent, less colored and almost non-toxic as easily assumed from the molecular structure. Therefore, they are expected to be usable without problems in the fields of application wherein contact with the human body is not avoidable, for example medical supplies such as disposable diapers, tampons, sanitary cotton, bandages and napkins. Secondly, there is no fear of the gel structure being broken because of strong gel strength, even when they are used in a hydrated state for a long time. Consequently, they are preferably used for industrial uses such as water-absorbers for water-containing oils, other dehydrating agents and drying agents, and for water-retaining agents for plants or soils, carriers for chromatography and other uses requiring water absorbency and water retentivity. Thirdly, the gels are produced very easily on an industrial scale and besides they can be molded into optional shapes depending upon the intended use.

The hydrophilic gels of the present invention may contain coloring agents, perfumes, other additives and inorganic or organic fillers, unless their properties are adversely affected. Further, they may be used in combination with materials such as paper, fiber, cloth and the like.

The present invention will be illustrated in more detail with reference to the following examples, which are not intended to limit the present invention thereto.

The term "Part" in the examples means "Part by weight".

The water absorption ability in the examples is defined as follows:

$$\text{Water absorption ability} = \frac{\text{weight of gel after absorption}}{\text{weight of dry gel}}$$

EXAMPLE 1

Ten parts of polyvinyl alcohol (polymerization degree, 1750; saponification degree, 88%) was added to water (200 parts) in a polymerization vessel and dissolved in water with stirring. Potassium persulfate (0.135 part) was added, and then acrylic acid (16.4 parts) was added and polymerized at 60° C. for 1 hour with stirring. The resulting polymerization mixture was added to a solution of sodium hydroxide (13.5 parts) in methanol (1000 parts) and water (100 parts). The produced precipitate was collected, and heat treated with drying under reduced pressure at 80° C. for 5 hours and for additional 1 and 2 hours in a hot air of 120° C. The gel thus obtained had a water absorption ability of 709 for additional 1 hour's heat treatment, and 650 for additional 2 hours' heat treatment.

EXAMPLE 2

Ten parts of polyvinyl alcohol (polymerization degree, 1750; saponification degree, 88%) was added to water (200 parts) in a polymerization vessel and dissolved in water with stirring. Potassium persulfate (0.135 part was added, and then acrylic acid (16.4 parts) was added and polymerized at 60° C. for 1 hour with stirring. The resulting polymerization mixture was added to a solution of triethylamine (29 parts) in methanol (1000 parts). The produced precipitate was collected and, heat treated with drying under reduced pressure at 80° C. for 5 hours and for additional 1 and 2 hours in a hot air of 120° C. The gel thus obtained had a water absorption ability of 545 for additional 1 hour's heat treatment, and 453 for additional 2 hours' heat treatment.

EXAMPLE 3

Toluene (150 parts) was added to a polymerization vessel, and polyvinyl acetate (7 parts; polymerization degree, 2000) and sorbitan monostearate (0.9 part) were then dissolved in toluene. Polyvinyl alcohol (10 parts; polymerization degree, 1750; saponification degree, 88%), acrylic acid (16.4 parts) and potassium persulfate (0.135 part) were dissolved in water (100 parts), and the resulting solution was added dropwise to the toluene solution with stirring. Thereafter, polymerization was carried out by stirring the mixture at 60° C. for 2.5 hours and then at 75° C. for 1.5 hours. After polymerization, the polymer was filtered and added to methanol (500 parts), followed by stirring at room temperature for 30 minutes. After filtering, the polymer was heat treated with drying at 80° C. for 5 hours and for additional 30 minutes at 100° C. The polymer was then added to a solution of sodium hydroxide (13.5 parts) in methanol (500 parts) and water (50 parts), followed by stirring at room temperature for 30 minutes. The gel thus obtained was filtered, washed with methanol and dried. The gel had a water absorption ability of 393.

EXAMPLE 4

Ten parts of polyvinyl alcohol (polymerization degree, 1750; saponification degree, 99%) was added to water (200 parts) in a polymerization vessel and dissolved in water at 80° C. with stirring. The solution was cooled to room temperature, and potassium persulfate (0.135 part) was added thereto. Thereafter, acrylic acid (16.4 parts) and divinylbenzene (0.5 part) were added, and polymerization was carried out at 60° C. for 1 hour with stirring. The resulting polymerization mixture was added to a solution of sodium hydroxide (13.5 parts) in methanol (1000 parts) and water (100 parts). The produced precipitate was collected and heat treated with drying under reduced pressure at 80° C. for 5 hours and for additional 1 hour in a hot air of 120° C. The gel thus obtained had a water absorption ability of 220.

EXAMPLE 5

Ten parts of polyvinyl alcohol (polymerization degree, 1750; saponification degree, 88%) was added to water (200 parts) in a polymerization vessel and dissolved in water with stirring. Potassium persulfate (0.2 part) was added, and then sodium acrylate (21.6 parts) was added and polymerized at 60° C. for 5 hours with stirring. The resulting polymerization mixture was added to methanol (1000 parts), and the produced precipitate was collected and heat treated with drying under reduced pressure at 80° C. for 5 hours and for additional 1 hour in a hot air of 120° C. The gel thus obtained had a water absorption ability of 480.

EXAMPLE 6

Ten parts of polyvinyl alcohol (polymerization degree, 1750; saponification degree, 88%) was added to water (200 parts) in a polymerization vessel and dissolved in water with stirring, and potassium persulfate (0.2 part) was added thereto. Thereafter, potassium acrylate (25 parts) and divinylbenzene (0.5 part) were added, and polymerization was carried out at 60° C. for 5 hours with stirring. The resulting polymerization mixture was added to methanol (1000 parts), and the produced precipitate was collected and heat treated with drying under reduced pressure at 80° C. for 5 hours and for additional 1 hour in a hot air of 120° C. The gel thus obtained had a water absorption ability of 180.

EXAMPLE 7

Ten parts of polyvinyl alcohol (polymerization degree, 1750; saponification degree, 99%) was added to water (200 parts) in a polymerization vessel and dissolved in water at 80° C. with stirring. The solution was cooled to room temperature, and potassium persulfate (0.135 part) was added thereto. Thereafter, ammonium acrylate (20 parts) was added and polymerized at 60° C. for 5 hours with stirring. The resulting polymerization mixture was added to methanol (1000 parts), and the produced precipitate was collected and heat treated with drying under reduced pressure at 80° C. for 5 hours and for additional 30 minutes in a hot air of 120° C. The gel thus obtained had a water absorption ability of 450.

What we claim is:

1. A method for producing a hydrophilic gel comprising polymerizing acrylic acid and/or methacrylic acid in the presence of polyvinyl alcohol to obtain a polymer (A) which is then subjected to neutralization followed by heat treatment or to heat treatment followed by neutralization, or polymerizing a neutralized product of acrylic acid and/or methacrylic acid in the presence of polyvinyl alcohol to obtain a polymer (B) which is then subjected to heat treatment, wherein said polymerization is carried out in an aqueous solution having a total concentration of acrylic acid and/or methacrylic acid or its neutralized product (the weight of the neutralized product is converted to the acid basis) and polyvinyl alcohol of 10 to 60% by weight, said heat treatment temperature is 50° to 150° C., and the weight ratio of polyvinylalcohol to acrylic acid and/or methacrylic acid or its salt (the weight of the neutralized product is converted to the acid basis) is 10 to 90:90 to 10.

2. A method according to claim 1, wherein the carboxylic acid group of the neutralized product of the polymer (A), acrylic acid or methacrylic acid is represented by the formula,

wherein $R_1$ is a sodium or potassium atom,

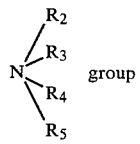

(in which $R_2$, $R_3$, $R_4$ and $R_5$ are each hydrogen atom, $C_1$–$C_4$ alkyl or alkanol group, phenyl group, $C_7$–$C_8$ aralkyl or aryl group and at least one of them is a hydrogen atom) or

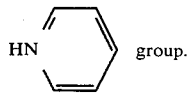

3. A method according to claim 2, wherein $R_1$ is a sodium or potassium atom or ammonium group.

4. A method according to claim 3, wherein $R_1$ is a sodium atom.

5. A method according to claim 1, wherein the weight ratio is 12 to 88:88 to 12.

6. A method according to claim 1, wherein the total concentration is 12 to 50% by weight.

7. A method according to claim 1, wherein the aqueous solution is dispersed in a water-insoluble organic solvent.

8. A method according to claim 1, wherein the temperature of heat treatment is 60° to 120° C.

9. A method according to claim 1, wherein said polymer (A) is neutralized with an alkali selected from the group consisting of sodium hydroxide, potassium hydroxide, ammonia and an organic amine.

10. A method according to claim 9, wherein the polymer (A) is neutralized with sodium hydroxide or potassium hydroxide.

11. A method according to claim 9, wherein the neutralization agent is an organic amine member selected from the group consisting of methylamine, dimethylamine, trimethylamine, ethylamine, diethylamine, triethylamine, n-propylamine, isopropylamine, di-n-propylamine, di-isopropylamine, tri-n-propylamine, tri-isopropylamine, tert-butylamine, n-butylamine, isobutylamine, di-tert-butylamine, d-n-butylamine, di-isobutylamine, tri-tert-butylamine, tri-isobutylamine, tri-n-butylamine, monoethanolamine, diethanolamine, triethanolamine, monoisopropanolamine, diisopropanolamine, triisopropanolamine, cyclohexylamine, benzylamine, aniline and pyridine.

12. A method according to claim 1, wherein the polymerization for obtaining said polymer (A), or said polymer (B) is carried out adding a crosslinking agent in amount of 0.0001 to 20 mole % based on the amount of acrylic acid and/or methacrylic acid, or its salt.

13. A hydrophilic gel obtained by the method according to claim 1.

14. A hydrophilic gel prepared by the method of claim 2.

15. A hydrophilic gel prepared by the method of claim 5.

16. A hydrophilic gel prepared by the process of claim 12.

* * * * *